United States Patent [19]

Baba et al.

[11] Patent Number: 5,118,862

[45] Date of Patent: Jun. 2, 1992

[54] PROCESS FOR PRODUCING α,β-UNSATURATED CARBONYL COMPOUND

[75] Inventors: Toshihide Baba, Takatsuki; Mitsuo Masai, Nishinomiya, both of Japan

[73] Assignee: Nippon Zeon Co., Ltd., Tokyo, Japan

[21] Appl. No.: 572,581

[22] Filed: Aug. 27, 1990

[30] Foreign Application Priority Data

Aug. 30, 1989 [JP] Japan ................... 1-224033

[51] Int. Cl.$^5$ ............................................ C07C 45/37
[52] U.S. Cl. ...................... 568/356; 568/360; 568/398; 568/399; 568/319; 568/320
[58] Field of Search ............... 568/398, 356, 399, 360, 568/405, 361, 319, 320

[56] References Cited

U.S. PATENT DOCUMENTS 3,153,083 10/1964 Smidt et al. ...................... 568/398
3,365,498 1/1968 Bryant et al. ..................... 568/401
3,461,157 8/1969 Olivier et al. .................... 568/401

OTHER PUBLICATIONS

"Journal of Organic Chemistry" vol. 43, No. 5, 1978.
Ito et al., J. Org. Chem., vol. 43, pp. 1011-1012 (1978).
Chemical Abstracts, vol. 113, No. 25, Abstract No. 230818D.
Chemical Communications, No. 22, pp. 1697-1699, Nov. 22, 1989.
Journal of Organic Chemistry, vol. 43, No. 5, pp. 1011-1013, 1978.

*Primary Examiner*—James H. Reamer
*Attorney, Agent, or Firm*—Birch, Stewart, Kolasch & Birch

[57] ABSTRACT

Disclosed is a process for producing an α,β-unsaturated carbonyl compound represented by the formula [II]:

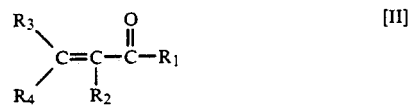

wherein $R_1$, $R_2$, $R_3$ and $R_4$ each represents a hydrogen atom or a hydrocarbon residue and may be linear or may form a ring in optional combination thereof and total carbon atom number of $R_1$, $R_2$, $R_3$ and $R_4$ is 12 or less, which comprises contacting oxygen with an alkenyl compound represented by the formula [I]:

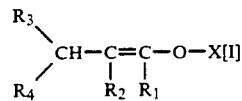

wherein $R_1$, $R_2$, $R_3$ and $R_4$ are as defined above and X represents a trihydrocarbylsilyl group or an acyl group in the presence of a platinum group metal-supporting catalyst.

20 Claims, No Drawings

PROCESS FOR PRODUCING α,β-UNSATURATED CARBONYL COMPOUND

BACKGROUND OF THE INVENTION

1. Field of the Invention

The present invention relates to a novel process for producing an α,β-unsaturated carbonyl compound and more particularly, it relates to a process for producing an α,β-unsaturated carbonyl compound by reacting an alkenyl compound with oxygen in heterogeneous system.

2. Related Art

Unsaturated carbonyl compounds such as cyclopentenone derivatives, cyclohexenone derivatives and cyclododecenone derivatives are useful chemical substances in the field of perfumes, medicines and chemicals.

As a process for synthesizing of these unsaturated carbonyl compounds, it has been known to react an alkenylsilyl ether with palladium acetate ("Journal of Organic Chemistry", 1978, 43, 1011). However, this process is not economical as expensive palladium is used in a stoichiometric amount. Moreover, the reaction is carried out in a homogeneous system and so recovery of palladium from the reaction system takes trouble and this process is inferior in operability.

SUMMARY OF THE INVENTION

As a result of the intensive research conducted by the inventors in an attempt to solve the above problems, it has been found that unsaturated carbonyl compounds can be obtained more economically and with superior operability by contacting an alkenyl compound, such as alkenylsilyl ether, alkenyl ester or the like, with oxygen in the presence of a platinum group metal-supporting catalyst. The present invention has been accomplished based on this finding.

Thus, the present invention provides a process for producing an α,β-unsaturated carbonyl compound represented by the following formula [II], characterized by contacting an alkenyl compound represented by the following formula [I] with oxygen in the presence of a platinum group metal-supporting catalyst.

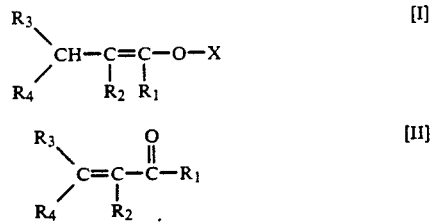

(wherein $R_1$, $R_2$, $R_3$ and $R_4$ each represents a hydrogen atom or a hydrocarbon residue and may be linear or may form ring in optional combination and total carbon atom number of $R_1$, $R_2$, $R_3$ and $R_4$ is 12 or less, and X represents a trihydrocarbylsilyl group or an acyl group).

DETAILED DESCRIPTION OF PREFERRED EMBODIMENTS

In the present invention, alkenyl compounds represented by the above formula [I] are used as starting materials. In the formula, $R_1$ represents a hydrogen atom, an alkyl group such as methyl group, ethyl group, propyl group, pentyl group or the like, an alkylene group which may link to $R_2$, $R_3$ or $R_4$ to form a ring such as cyclopentane ring, cyclohexane ring, cyclododecane ring or the like, or an aryl group such as phenyl group, trityl group or the like and $R_2$, $R_3$ and $R_4$ each represents a hydrogen atom or the same alkyl, alkylene or aryl group as of $R_1$. These $R_1$, $R_2$, $R_3$ and $R_4$ may form ring in optional combination of them such as cycloalkyl group, cycloalkenyl, phenyl group, fused ring or the like. The total carbon atom number of $R_1$, $R_2$, $R_3$ and $R_4$ is 12 or less.

X represents a trihydrocarbylsilyl group such as trimethylsilyl group, triethylsilyl group, tripropylsilyl group, tributylsilyl group or the like or an acyl group such as formyl group, acetyl group, propionyl group, butyryl group, valeryl group or the like.

As examples of these alkenyl compounds, mention may be made of alkenylsilyl ethers such as 1-cyclopentenyltrimethylsily ether, 1-cyclohexenyltrimethylsilyl ether, 2-methyl-1-cyclopentenyltrimethylsilyl ether, 1-cyclopentenyltriethylsilyl ether, 1-cyclopentenyltripropylsilyl ether, 2-(2-pentenyl)-1-cyclohexenyltrimethylsilyl ether, 2-propyl-1-cyclopentenyltrimethylsilyl ether, 2-pentyl-1-cyclohexenyltrimethylsilyl ether, 2-(2-pentenyl)-1-cyclopentenyltrimethylsilyl ether, 2-(2-pentynyl)-1-cyclopentenyltrimethylsilyl ether, 1-pentyl-1-butenyltrimethylsilyl ether, 1-propenyltrimethylsilyl ether, 1-pentenyltrimethylsilyl ether, 2-methyl-1-butenyltrimethylsilyl ether, and 3-phenyl-1-propenyltrimethylsilyl ether, and alkenyl esters such as 1-cyclopentenyl acetate, 1-cyclohexenyl acetate, 2-methyl-1-cyclopentenyl acetate, 2-ethyl-1-cyclopentenyl acetate, 1-cycloheptenyl acetate, 1-cyclopentenyl propionate, 1-cyclopentenyl butyrate, 1-phenyl-1-butenyl acetate, 1-propenyl acetate, 1-hexenyl acetate, 3-methyl-1-butenyl acetate, and 3-phenyl-1-propenyl acetate.

Synthesis of these compounds may be carried out in accordance with conventional process. For example, 1-cyclopentenyltrimethylsilyl ether can be easily synthesized by reacting cyclopentanone with trimethylsilyl chloride in the presence of a base. Furthermore, 1-cyclopentenyl acetate can be easily synthesized by reacting cyclopentanone with isopropenyl acetate in the presence of an acid or by reacting cyclopentanone with acetic anhydride.

The process of the present invention is carried out by contacting an alkenyl compound with oxygen in the presence of a platinum group metal-supporting catalyst.

Oxygen may be supplied in a gaseous form to reaction system or may be previously dissolved in reaction system. Furthermore, if necessary, oxygen may also be used in admixture with an inert gas such as nitrogen. Amount of oxygen used is usually 0.4-5 mols, preferably 0.4-2 mols per 1 mol of alkenyl compound.

Platinum group metal-supporting catalysts used in the present invention are those which comprise a carrier on which a platinum group metal is supported. The platinum group metals include, for example, palladium, platinum, rhodium, iridium, and ruthenium. Carriers include, for example, porous materials such as oxides such as silica, alumina, titanium oxide, and zeolite or active carbon.

Platinum group metal is supported on a carrier by conventional method. For example, there is a method according to which with an aqueous solution of a salt of the above platinum group metal is impregnated a carrier and calcined and then reduced. Amount of the platinum group metal supported on a carrier is not critical, but usually is 0.1–15% by weight. Amount of platinum group metal-supporting catalyst used is usually 0.01–0.5 g atom per 1 mol of alkenyl compound.

Reaction conditions may vary depending on kinds of starting material and catalyst, but usually are reaction temperature: 0° C. or higher, preferably 20°–100° C. and reaction time: 10 minutes–72 hours.

In carrying out the reaction, preferably a diluent is allowed to be used for improvement of selectivity. Examples of the diluent are N-methyl-pyrrolidone, dimethylformamide, dimethylacetamide, tetrahydrofuran and dioxane. These diluents are normally used in such a proportion as providing a concentration of starting material of 1–50% by weight.

Since the reaction of the present invention is carried out in a heterogeneous system, catalyst can be easily separated by filtration of the reaction mixture after completion of the reaction. The filtrate can be purified by operations such as distillation and extraction to give a high purity $\alpha,\beta$-unsaturated carbonyl compound, namely, $\alpha,\beta$-unsaturated ketone or $\alpha,\beta$-unsaturated aldehyde as an objective product. Such unsaturated carbonyl compounds are used as intermediates for preparation of useful compounds, especially intermediates for perfumes and medicines.

Thus, according to the present invention, $\alpha,\beta$-unsaturated carbonyl compounds can be obtained in a high yield in economical and superior manner as compared with conventional technique.

The present invention will be explained in more detail by the following non-limiting examples. Parts and percents in examples, comparative examples and reference examples are all by weight unless otherwise notified.

Reference Example 1 Preparation of catalyst $2.5 \times 10^{-3}$ mol of tetramminepalladium (II) chloride ([Pd(NH$_3$)$_4$]Cl$_2$) was dissolved in 100 ml of 28% aqueous ammonia and in the solution was dipped 10 g of silica (trade name Grade 62 manufactured by Fuji Davidson Co.). Then, the silica was calcined in the air for 1 hour at 180° C. and then reduced with hydrogen gas at 360° C. for 1 hour to obtain 9.6 g of a palladium (0 valence)-supporting silica catalyst.

Weight ratio of the supported palladium based on silica was 4.2% which was obtained by atomic absorption spectrometry.

EXAMPLE 1

1.12 mmol of 1-cyclopentenyltrimethylsilyl ether, 0.3 g of the palladium-supporting silica catalyst (amount of palladium supported: 4.2% by weight of silica), and 4 ml of N-methyl-2-pyrrolidone were charged in a vessel and stirred in oxygen atmosphere at 60° C. for 24 hours. After completion of reaction, reaction mixture was analyzed by gas chromatography to find that 2-cyclopentenone was generated in a yield of 90.1% and at a selectivity of 99.2%. The reaction mixture was filtered to remove catalyst and the filtrate was distilled under reduced pressure to obtain 2-cyclopentenone in a yield of 82%.

Comparative Example 1

Example 1 was repeated except that nitrogen atmosphere was employed in place of oxygen atmosphere. Yield of 2-cyclopentenone in reaction mixture was 6.3% and selectivity was 14.6%.

Comparative Example 2

Example 1 was repeated except that the catalyst used was prepared in the same manner as in Reference Example 1 except that the reduction with hydrogen gas was not conducted. Yield of 2-cyclopentenone in the reaction mixture was 2.2% and selectivity was 2.9%. Principal product was cyclopentanone (yield 72.6%).

EXAMPLE 2

Example 1 was repeated except that 1-cyclohexenyltrimethylsilyl ether was used in place of 1-cyclopentenyltrimethylsilyl ether and amount of supported palladium was 3.9% by weight of silica. Yield of 2-cyclohexenone in the reaction mixture was 87.4% and selectivity was 82.3%.

EXAMPLE 3

Example 1 was repeated except that 1-cyclopentenyl acetate was used in place of 1-cyclopentenyltrimethylsilyl ether. Yield of 2-cyclopentenone in the reaction mixture was 64.1% and selectivity was 98.4%. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for producing an $\alpha,\beta$-unsaturated carbonyl compound represented by the formula [II]:

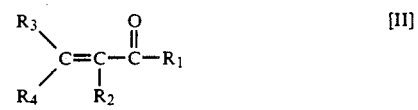

wherein R$_1$, R$_2$, R$_3$, and R$_4$ each represents a hydrogen atom, an alkyl group, an alkylene group, or an aryl group and any two of R$_1$ —R$_4$ may combine to form a ring, and wherein the total carbon atom number of R$_1$, R$_2$, R$_3$, and R$_4$ is 12 or less, which comprises contacting oxygen with an alkenyl compound represented by the formula [I]:

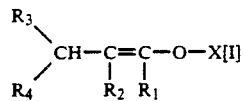

wherein R$_1$, R$_2$, R$_3$, and R$_4$ are as defined above and X represents a trihydrocarbylsilyl group or an acyl group, in the presence of a platinum group metal-supporting catalyst wherein said platinum group metal is in the metallic state.

2. A process according to claim 1, wherein the alkenyl compound is a linear or a cyclic olefin compound.

3. A process according to claim 1, wherein X in the formula [I] represents a trialkylsilyl group or an acyl group.

4. A process according to claim 1, wherein oxygen is supplied in gaseous form to the reaction.

5. A process according to claim 1, wherein the amount of oxygen is 0.4–5 mols per 1 mol of the alkenyl compound.

6. A process according to claim 1, wherein the platinum group metal is palladium, platinum, rhodium, iridium or ruthenium.

7. A process according to claim 6, wherein the platinum group metal is palladium.

8. A process according to claim 1, wherein the carrier of the catalyst is a porous material of inorganic compound.

9. A process according to claim 8, wherein the porous material is silica, alumina, titanium oxide, zeolite or active carbon.

10. A process according to claim 9, wherein the porous material is silica.

11. A process according to claim 1, wherein the amount of platinum group metal supported is 0.1–15% by weight.

12. A process according to claim 1, wherein the amount of the platinum group metal-supporting catalyst is 0.01–0.5 g atom per 1 mol of the alkenyl compound.

13. A process according to claim 1, wherein the reaction temperature is 0° C.–100° C.

14. A process according to claim 1, wherein the reaction time is 10 minutes–72 hours.

15. A process according to claim 1, wherein the reaction is carried out in the presence of a diluent.

16. A process according to claim 15, wherein the diluent is an amide or an ether.

17. A process according to claim 15, wherein the diluent is N-methylpyrrolidone, dimethylformamide or dimethylacetamide.

18. A process according to claim 15, wherein the amount of the diluent is selected so that concentration of starting material is 1–50% by weight.

19. A process according to claim 1, wherein oxygen is supplied to the reaction by dissolved oxygen.

20. A process for producing an $\alpha,\beta$-unsaturated carbonyl compound represented by the formula (II):

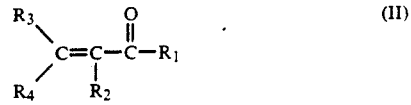

wherein $R_1$, $R_2$, $R_3$, and $R_4$ each represents a hydrogen atom or a hydrocarbon residue and may be linear or may form a ring in optional combination thereof and the total carbon atom number of $R_1$, $R_2$, $R_3$, and $R_4$ is 12 or less, which comprises contacting oxygen with an alkenyl compound represented by the formula (I):

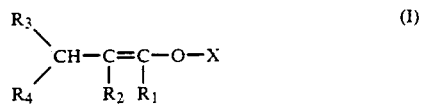

wherein $R_1$, $R_2$, $R_3$, and $R_4$ are as defined above and X represents a trihydrocarbylsilyl group or an acyl group, in the presence of a platinum group metal-supporting catalyst wherein said platinum group metal is in the metallic state.

* * * * *